United States Patent
Zheng et al.

(10) Patent No.: US 8,182,890 B2
(45) Date of Patent: May 22, 2012

(54) BIODEGRADABLE ENDOPROSTHESES AND METHODS FOR THEIR FABRICATION

(75) Inventors: Xiaoxia Zheng, Mountain View, CA (US); John Yan, Los Gatos, CA (US); Vinayak Bhat, Cupertino, CA (US)

(73) Assignee: Elixir Medical Corporation, Sunnyvale, CA (US)

(*) Notice: Subject to any disclaimer, the term of this patent is extended or adjusted under 35 U.S.C. 154(b) by 1069 days.

(21) Appl. No.: 12/016,085

(22) Filed: Jan. 17, 2008

(65) Prior Publication Data

US 2008/0177374 A1   Jul. 24, 2008

Related U.S. Application Data

(60) Provisional application No. 60/885,700, filed on Jan. 19, 2007.

(51) Int. Cl.
*B29D 23/00* (2006.01)
*A61F 2/04* (2006.01)

(52) U.S. Cl. ............... 428/36.9; 428/34.1; 623/1.15; 264/209.1

(58) Field of Classification Search .......... 428/34.1, 428/36.9; 623/1.15, 1.49, 1.38; 264/209.1; 606/154
See application file for complete search history.

(56) References Cited

U.S. PATENT DOCUMENTS

| | | | |
|---|---|---|---|
| 3,867,190 A * | 2/1975 | Schmitt et al. | 427/2.25 |
| 5,441,483 A | 8/1995 | Avitall | |
| 5,447,724 A | 9/1995 | Helmus et al. | |
| 5,670,161 A | 9/1997 | Healy et al. | |
| 5,674,286 A | 10/1997 | D'Alessio et al. | |
| 5,741,329 A | 4/1998 | Agrawal et al. | |
| 5,980,564 A | 11/1999 | Stinson | |
| 6,190,405 B1 | 2/2001 | Culombo et al. | |
| 6,224,803 B1 | 5/2001 | Tiernan | |
| 6,245,103 B1 | 6/2001 | Stinson | |
| 6,585,755 B2 | 7/2003 | Jackson et al. | |
| 6,626,939 B1 | 9/2003 | Burnside et al. | |
| 6,652,582 B1 | 11/2003 | Stinson | |
| 6,719,934 B2 | 4/2004 | Stinson | |
| 6,773,455 B2 | 8/2004 | Allen et al. | |
| 6,863,757 B1 | 3/2005 | Gonzalez et al. | |
| 6,896,695 B2 | 5/2005 | Mueller et al. | |
| 6,997,948 B2 | 2/2006 | Stinson | |
| 7,108,716 B2 | 9/2006 | Burnside et al. | |
| 7,258,697 B1 | 8/2007 | Cox et al. | |
| 7,279,005 B2 | 10/2007 | Stinson | |

(Continued)

FOREIGN PATENT DOCUMENTS

CN       1328853 A       1/2002

(Continued)

OTHER PUBLICATIONS

U.S. Appl. No. 12/016,077, filed Jan. 17, 2008; first named inventor: Howard Huang.

(Continued)

*Primary Examiner* — Rena Dye
*Assistant Examiner* — Yan Lan
(74) *Attorney, Agent, or Firm* — Wilson Sonsini Goodrich & Rosati

(57) ABSTRACT

Biodegradable endoprostheses are formed from amorphous polymers having desirable biodegradation characteristics. The strength of such amorphous polymers is enhanced by annealing to increase crystallinity without substantially increasing the biodegradation time.

54 Claims, 3 Drawing Sheets

U.S. PATENT DOCUMENTS

| | | | |
|---|---|---|---|
| 7,291,166 B2 | 11/2007 | Cheng et al. | |
| 7,354,450 B2 | 4/2008 | Bicek et al. | |
| 7,377,939 B2 | 5/2008 | Williams et al. | |
| 7,390,333 B2 | 6/2008 | Dutta | |
| 7,594,928 B2 * | 9/2009 | Headley et al. | 623/1.22 |
| 7,622,070 B2 | 11/2009 | Atladottir et al. | |
| 7,666,342 B2 | 2/2010 | Limon et al. | |
| 7,824,601 B1 | 11/2010 | Stankus et al. | |
| 7,829,008 B2 | 11/2010 | Gueriguian et al. | |
| 7,875,233 B2 | 1/2011 | Huang et al. | |
| 7,971,333 B2 | 7/2011 | Gale et al. | |
| 2001/0016769 A1 | 8/2001 | Hojeibane | |
| 2001/0016770 A1 | 8/2001 | Allen et al. | |
| 2003/0033007 A1 | 2/2003 | Sirhan et al. | |
| 2003/0064097 A1 | 4/2003 | Patel et al. | |
| 2003/0093143 A1 | 5/2003 | Zhao et al. | |
| 2003/0144726 A1 | 7/2003 | Majercak et al. | |
| 2003/0144729 A1 | 7/2003 | Bicek et al. | |
| 2003/0199993 A1 | 10/2003 | Gellman et al. | |
| 2003/0236320 A1 | 12/2003 | Martin et al. | |
| 2004/0073290 A1 | 4/2004 | Chouinard | |
| 2005/0031704 A1 | 2/2005 | Ahn | |
| 2005/0070991 A1 | 3/2005 | Pienknagura | |
| 2005/0075625 A1 * | 4/2005 | Dao et al. | 604/523 |
| 2005/0075716 A1 | 4/2005 | Yan | |
| 2005/0123588 A1 | 6/2005 | Zhu et al. | |
| 2005/0187615 A1 | 8/2005 | Williams et al. | |
| 2005/0232964 A1 | 10/2005 | Fennimore | |
| 2006/0111485 A1 | 5/2006 | Laghi | |
| 2006/0129222 A1 | 6/2006 | Stinson | |
| 2006/0147538 A1 | 7/2006 | Craig et al. | |
| 2006/0251618 A1 | 11/2006 | Dennis et al. | |
| 2006/0287710 A1 * | 12/2006 | Lendlein et al. | 623/1.19 |
| 2007/0253999 A1 | 11/2007 | Huang et al. | |
| 2007/0290412 A1 | 12/2007 | Capek et al. | |
| 2008/0177373 A1 | 7/2008 | Huang et al. | |
| 2009/0096137 A1 | 4/2009 | Williams et al. | |
| 2009/0146348 A1 | 6/2009 | Huang et al. | |
| 2009/0208555 A1 | 8/2009 | Kuttler et al. | |

FOREIGN PATENT DOCUMENTS

| | | | |
|---|---|---|---|
| CN | 1569270 A | | 1/2005 |
| WO | WO 92/04393 A1 | | 3/1992 |
| WO | WO 2004/080332 A2 | | 9/2004 |
| WO | WO2004/110515 | * | 12/2004 |
| WO | WO 2004/080332 A3 | | 4/2005 |
| WO | WO 2007/126599 A2 | | 11/2007 |
| WO | WO 2007/146354 A2 | | 12/2007 |
| WO | WO 2008/002479 A2 | | 1/2008 |
| WO | WO 2008/002636 A2 | | 1/2008 |
| WO | WO 2008/005390 A1 | | 1/2008 |
| WO | WO 2008/008416 A1 | | 1/2008 |
| WO | WO 2008/011048 A2 | | 1/2008 |
| WO | WO 2007/146354 A3 | | 2/2008 |
| WO | WO 2008/016667 A2 | | 2/2008 |
| WO | WO 2008/016696 A2 | | 2/2008 |
| WO | WO 2008/016696 A3 | | 3/2008 |
| WO | WO 2008/033263 A2 | | 3/2008 |
| WO | WO 2008/002636 A3 | | 4/2008 |
| WO | WO 2008/051867 | | 5/2008 |
| WO | WO 2007/126599 A3 | | 7/2008 |
| WO | WO 2008/051867 A3 | | 8/2008 |
| WO | WO 2008/002479 A3 | | 9/2008 |
| WO | WO 2008/016667 A3 | | 11/2008 |
| WO | WO 2008/137821 A1 | | 11/2008 |
| WO | WO 2008/011048 A3 | | 3/2009 |
| WO | WO 2008/033263 A3 | | 4/2009 |

OTHER PUBLICATIONS

International Search Report and Written Opinion of PCT Application No. PCT/US08/51497, dated Aug. 1, 2008, 8 pages total.

International Search Report and Written Opinion of PCT Application No. PCT/US08/51479, dated Aug. 1, 2008, 9 pages total.

Weir, et al. Processing, Annealing and Sterilisation of Poly-L-Lactide. Biomaterials. 2004; 25:3939-3949.

* cited by examiner

BIODEGRADABLE ENDOPROSTHESES AND METHODS FOR THEIR FABRICATION

CROSS-REFERENCES TO RELATED APPLICATIONS

This application claims the benefit of provisional application 60/885,700, filed on Jan. 19, 2007, the full disclosure of which is incorporated herein by reference.

BACKGROUND OF THE INVENTION

1. Field of the Invention

The present invention relates generally to medical devices and methods for their fabrication. In particular, the present invention relates to the fabrication of biodegradable endoprostheses, such as stents, having enhanced strength and controlled persistence after implantation.

Stents are generally tubular-shaped devices which function to hold open or reinforce a segment of a blood vessel or other body lumen, such as a coronary artery, carotid artery, saphenous vein graft, or femoral artery. They also are suitable to support and hold back a dissected arterial lining that could occlude the body lumen, to stabilize plaque, or to support bioprosthetic valves. Stents can be formed from various materials, particularly polymeric and/or metallic materials, and may be non-degradable, biodegradable, or be formed from both degradable and non-degradable components. Stents are typically delivered to the target area within the body lumen using a catheter. With balloon-expandable stents, the stent is mounted to a balloon catheter, navigated to the appropriate area, and the stent is expanded by inflating the balloon. A self-expanding stent is delivered to the target area and released, expanding to the required diameter to treat the disease. Stents may also elute various drugs and pharmacological agents.

Of particular interest to the present invention, biodegradable stents and other endoprostheses are usually formed from polymers which degrade by hydrolysis and other reaction mechanisms in the vascular or other luminal environment over time. Usually, it will be desirable to have the endoprosthesis completely degrade after it has served its needed supporting function in the body lumen. Typically, complete degradation will be desired in less than two years, often less than one year, and frequently in a matter of months after implantation. Many biodegradable endoprostheses, however, are persistent for longer than needed, often remaining in place long after the supporting or drug delivery function has ended. The extended persistence of many biodegradable endoprostheses often results from a desire to enhance their strength. The polymer construction materials are often strengthened, such as by incorporating materials having a higher crystallinity, so that they provide desired support but take longer to degrade than would otherwise be desirable.

For these reasons, it would be desirable to provide improved endoprostheses and methods for their fabrication, where the endoprostheses have a controlled strength and persistence. In particular, it would be desirable to be able to enhance the strength of certain biodegradable materials so that they have an improved strength when incorporated into stents and other endoprostheses without substantially lengthening their degradation periods. Moreover, it would be desirable to allow for control of the degradation period in the fabrication process so that an endoprosthesis can be made with different degradation periods while retaining an enhanced strength. At least some of these objectives will be met by the inventions described below.

2. Description of the Background Art

Heat annealing and other treatments of filaments and other components used in stents are described in U.S. Pat. No. 5,980,564, U.S. Pat. No. 6,245,103, and U.S. Pat. No. 6,626,939. Heat treatment of polymeric stent coatings is described in commonly owned, copending application no. PCT/US07/81996, which designates the United States.

BRIEF SUMMARY OF THE INVENTION

The present invention provides improved biodegradable endoprostheses and methods for their fabrication. The endoprostheses are formed from an amorphous, biodegradable polymer. The use of amorphous polymers is desirable since they provide relatively short periods of biodegradation, usually less than two years, often less than one year, frequently less than nine months, and sometimes shorter than six months, or even shorter. The present invention relies on modifying the amorphous polymers to introduce a desired degree of crystallinity. It has been found by inventors herein that introducing crystallinity into the amorphous polymer increases the strength of the polymer so that it is suitable for use as an endoprosthesis without substantially lengthening the period of biodegradation after implantation.

The crystallinity of a highly amorphous polymer as defined will be below 10% prior to modification. After modification, the crystallinity will usually be increased by at least 20% of the original crystallinity of the amorphous material, preferably by at least 100% of the original crystallinity of the amorphous material and more preferably by at least 1000% of the original crystallinity of the amorphous material. Presently preferred polymer materials will have a crystallinity in the range from 10% to 20% after modification as described herein below. As used herein, "crystallinity" refers to a degree of structural order or perfection within a polymer matrix.

Crystallinity can be measured by differential scanning calorimetry (Reading, M. et al, Measurement of crystallinity in polymers using modulated temperature differential scanning calorimetry, in Material Characterization by Dynamic and Modulated Thermal Analytical Techniques, ASTM STP 1402, Riga, A. T. et al. Ed, (2001) pp. 17-31.

Methods according to the present invention for fabricating biodegradable prostheses comprise providing a tubular body having an initial diameter, where the tubular body is composed at least partially of a substantially amorphous, biodegradable polymer. The tubular body is heated to a temperature above its glass transition temperature and below its melting point. The tubular body is then cooled to increase the crystallinity of the polymer. Either before or after this annealing process, the tubular body may be patterned into a structure capable of radial contraction and expansion in order to provide a stent or other endoprosthesis.

Usually, the tubular body will be fabricated as part of the method. Fabrication can be by a variety of conventional processes, such as extrusion, molding, dipping, and the like. A preferred formation process comprises spraying a polymer dissolved in a solvent onto a cylindrical mandrel or other structure. Optionally, additives, such as strength-enhancing materials, drugs, or the like, may be dissolved in the solvent together with the polymer so that the materials are integrally or monolithically formed with the endoprosthesis tube. Alternatively, the methods could rely on obtaining a pre-formed polymer tube from a supplier or other outside source.

The polymeric tubular body is usually formed as a substantially continuous cylinder free from holes or other discontinuities. The tubular body typically has an outside diameter in the range from 2 mm to 10 mm, a thickness in the range from 0.01 mm to 0.5 mm, and may be cut into lengths suitable for individual endoprostheses, typically in the range from 5 mm to 40 mm.

The tubular bodies may be formed from any amorphous polymer having desired degradation characteristics where the polymer may be modified to have the desired strength characteristics in accordance with the methods of the present invention. Exemplary amorphous polymers include poly-DL-Lactide, polylactide-co-glycolactide; polylactide-co-polycaprolactone, poly (L-lactide-co-trimethylene carbonate), polytrimethylene carbonate and copolymers; polyhydroxybutyrate and copolymers; polyhydroxyvalerate and copolymers, poly orthoesters and copolymers, poly anhydrides and copolymers, polyiminocarbonates and copolymers and the like. A particularly preferred polymer comprises a copolymer of L-lactide and glycolide, preferably with a weight ratio of 85% L-lactide to 15% glycolide.

The heating segment of the annealing process will typically be carried out for a period of from 1 minute to 3 hours, and the cooling will be typically to a temperature at or below ambient. Other suitable temperatures and times, however, are described in the Detailed Description of the Invention, below.

The tubular body will be patterned into a suitable endoprosthesis structure, typically by laser cutting or other conventional processes. The patterning will usually be performed after the annealing process, but could be performed before the annealing process. As a further alternative it may be desirable to anneal the tubular body both before and after the patterning, and in some instances additional annealing steps may be performed so that the stent could be subjected to three, four, or even more annealing steps during the fabrication process. In another embodiment the percentage residual monomer or oligomer of the biodegradable polymer stent material is equal or less than 3%, preferably less than 1%, more preferably less than 0.1%.

The endoprosthesis pattern can be any suitable pattern of the type employed in conventional endoprostheses. A variety of exemplary patterns are set forth in commonly owned, co-pending application Ser. No. 12/016,077, filed on the same day as the present application, the full disclosure of which is incorporated herein by reference.

In addition to the fabrication methods, the present invention also provides biodegradable prostheses comprising a tubular body composed at least partially of a substantially amorphous, biodegradable polymer. The biodegradable polymer will have been treated to produce spherulite crystals in the amorphous polymer to increase crystallinity by at least 20% of the original crytallinity. Other preferred aspects of the prosthesis have been described above with respect to the methods of fabrication.

DETAILED DESCRIPTION OF THE INVENTION

Figure 1:
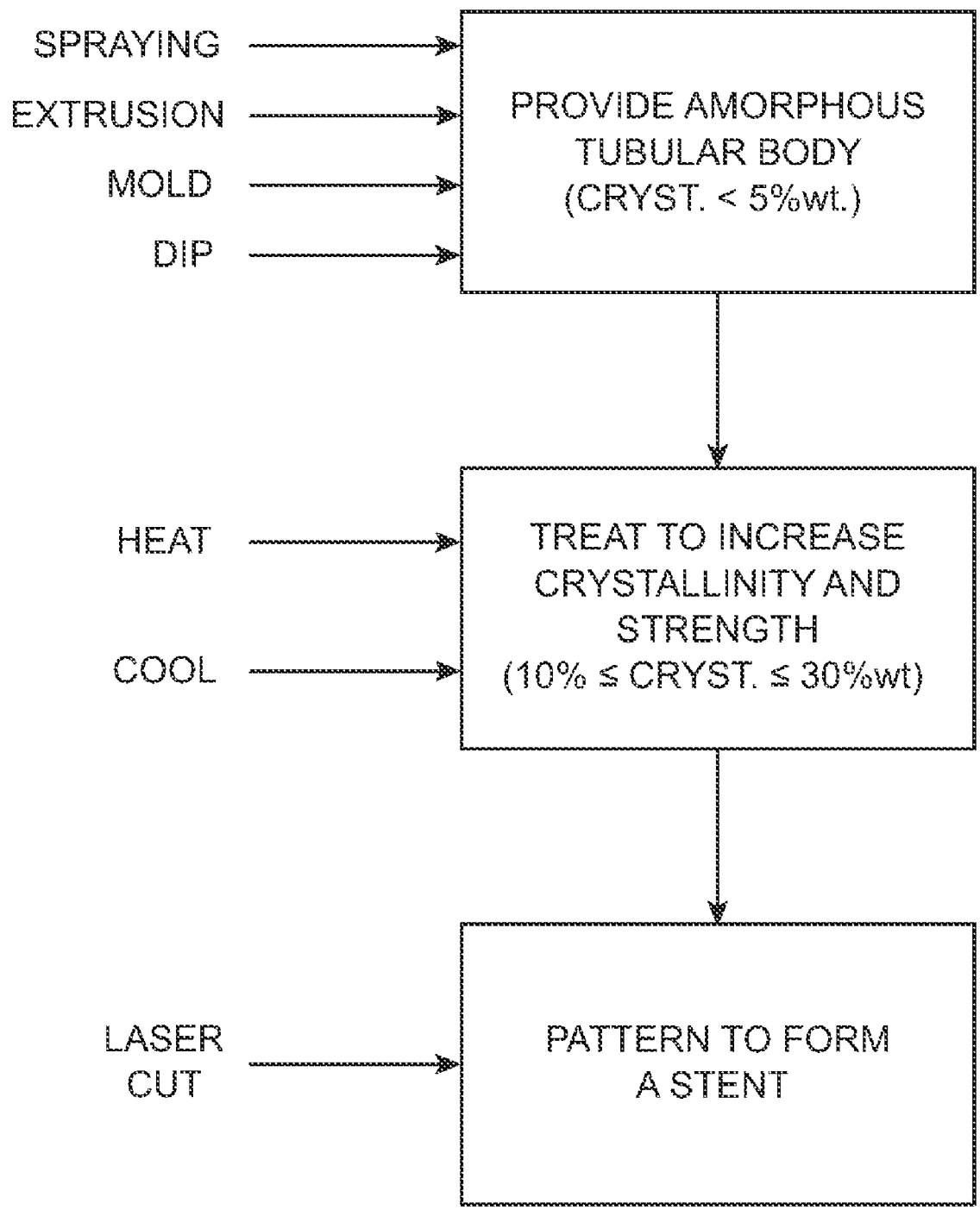
FIG. 1 is a block diagram illustrating the principal steps of the methods of the present invention.

Amorphous biodegradable polymers (less than 10% crystallinity) degrade faster than crystalline polymers but are weaker than crystalline polymers and hence are not typically suitable for vascular implants, such as stents, which need sufficient strength to provide support to the blood vessel. The present invention provides for the modification of amorphous polymeric materials to make them suitable for use as biodegradable stents and other endoprostheses. Amorphous materials suitable for modification according to the present invention include but are not limited to poly-DL-Lactide, polylactide-co-glycolactide; polylactide-co-polycaprolactone, poly (L-lactide-co-trimethylene carbonate), polytrimethylene carbonate and copolymers; polyhydroxybutyrate and copolymers; polyhydroxyvalerate and copolymers, poly orthoesters and copolymers, poly anhydrides and copolymers, polyiminocarbonates and copolymers and the like. The biodegradable polymeric stent material in this invention can be homopolymers, copolymers, graft polymer, block polymers, polymers with special functional groups or end groups such as acidic or hydrophilic type or a blend of two or more homopolymers or copolymers. An exemplary stent is made from amorphous material of a copolymer of 85/15 Poly(L-Lactide-co-Glycolide) and processed to increase crystallinity by at least 20% or original crystallinity, preferably by at least 100%, more preferably by at least 1000% of original crystallinity In one embodiment, the biodegradable stem substantially degrades in less than 2 years, preferable less than 1 year, more preferable less than 9 months.

In one embodiment, the biodegradable polymeric stent material includes, but is not limited to, polyesters, polyanhydrides, polyamides, polyurethanes, poly(ester urethane), polyureas, polyethers, polyalkylene carbonates, polyacrylic acids, polyamines, polyester amides, polyester amines, polyvinylacetate, polyethylene imine, polycyanoacrylates, polyphosphazenes, polyphosphates, polyphosphates, polyurethanes, polyureas, polysulfonates, polysulfonamides, polylactides, polyglycolides, regenerated cellulose, or biopolymers or blends, block polymers, copolymers or combinations thereof. Examples of these polymers include but are not limited to poly(L-lactic acid), poly(L/D-lactic acid), poly(L/DL-lactic acid), poly(glycolic acid), poly(lactide-co-glycolide), and copolymers and isomers, polydioxanone, poly(ethyl glutamate), poly(hydroxybutyrate), polyhydroxyvalerate and copolymer poly(3-hydroxy butyrate-co-hydroxy valerate), polycaprolactone, polyanhydride, poly(ortho esters); poly(ether esters), poly(trimethyl carbonate), poly(L-lactic acid-co-trimethylene carbonate), poly(L/D-lactic acid-co-trimethylene carbonate), poly(L/DL-lactic acid-co-trimethylene carbonate), poly(caprolactone-co-trimethylene carbonate), poly(glycolic acid-co-trimethylene carbonate), poly(glycolic acid-co-trimethylene carbonate-co-dioxanone), polyethylene carbonate, copolymers of polyethylene carbonate and poly(trimethylene carbonate), polypropylene carbonate, poly(iminocarbonates), poly(malic acid), modified poly(ethylene terephthalate), poly(butylene succinate), poly(butylene succinate adipate), poly(butylene succinate terephthalate), poly(butylene adipate-co-terephthalate), starch based polymers, hyaluronic acid, oxidized or non-oxidized regenerated cellulose copolymers and other aliphatic polyesters, or suitable copolymers thereof. The biodegradable polymeric stent material in this invention can be homopolymers, copolymers, graft polymer, block polymers, polymers with special functional groups or end groups such as acidic or hydrophilic type, or a blend of two or more homopolymers or copolymers.

In accordance with the present invention, the amorphous biodegradable polymeric material is processed to increase its crystallinity, Increased crystallinity may increase the strength, storage shelf life, and hydrolytic stability of the polymer stent material. The process initiates and/or enhances crystallinity in the polymeric material by nucleating and/or growing small size spherulite crystals in the material. Since the amorphous regions of the modified polymer are preferentially broken down by hydrolysis or enzymatic degradation in biological environment, the modified amorphous biodegradable polymer has increased crystallinity and increased material strength post processing. The increase in crystallinity can be achieved by 'Modifications' described in present invention which include at least one of heating, cooling, pressurizing, addition of additives, crosslinking and other processes.

The polymer material can be made into a tube by spraying, extrusion, molding, dipping or other process from a selected amorphous copolymer. The amorphous polymer tubing is optionally vacuumed to at least −25 in. Hg., annealed, and quenched to increase crystallinity. In one embodiment, the tube is vacuumed at or below 1 torr at ambient temperature to remove water and solvent. It is then annealed by heating to a temperature above the glass transitional temperature but below melting temperature of the polymer material. Preferably, the annealing temperature is at least 10° C. higher than the glass transitional temperature (Tg), more preferably being at least 20° C. higher, and still more preferably being at least 30° C. higher than the Tg. The annealing temperature is usually at least 5° C. below the melting point (Tm), preferably being at least 20° C. lower, and more preferably being at least 30° C. lower than the Tm of the polymer material. The annealing time is between 1 minute to 10 days, preferably from 30 minutes to 3 hours, and more preferably from 1.5 hours to 2.5 hours.

In one embodiment, the annealed tube is quenched by fast cooling from the annealing temperature to a temperature at or below ambient temperature over a period from 1 second to 1 hour, preferably 1 minute to 30 minutes, and more preferably 5 minutes to 15 minutes. In another embodiment the annealed tune is quenched by slow cooling from the annealing temperature to at or below ambient temperature within 1 hour to 24 hours, preferably 4 hours to 12 hours, and more preferably 6 hours to 10 hours. In some instances the heat treated tube is cooled to a temperature below ambient temperature for a period from 1 minute to 96 hours, more preferably 24 hours to 72 hours, to stabilize the crystals and/or terminate crystallization. This annealing and quenching process initiates and promotes nucleation of crystals in the polymer and increases the mechanical strength of the material. The initial annealing temperature and the cooling rate can be controlled to optimize the size of the crystals and strength of the material. In a further embodiment, the unannealed and/or annealed tube is exposed to ebeam or gamma radiation, with single or multiple doses of radiation ranging from 5 kGy to 100 kGy, more preferably from 10 kGy to 50 kGy.

The stent or other endoprosthesis is patterned from a tube of the stent material in an "expanded" diameter and subsequently crimped to a smaller diameter and fitted onto a balloon of a delivery catheter. The stent is patterned, typically by laser cutting, with the tubing diameter about 1 to 1.3 times, preferably 1.1 to 1.5 times, more preferably 1.15 to 1.25 times, larger the intended deployed diameter. For example, a stent cut at a 3.5 mm×18 mm outer diameter is crimped on a 3.0 mm×18 mm stent delivery catheter. In a further embodiment, the unannealed and/or annealed stent is exposed to ebeam or gamma radiation, with single or multiple doses of radiation ranging from 5 kGy to 100 kGy, more preferably from 10 kGy to 50 kGy.

The stent material may lose some crystallinity during stent cutting. In such cases, the stent annealed after cutting and/or a second time to re-crystallize the polymer to a higher crystallinity. Thus, the cut stent may be annealed a second time as generally described above. Annealing followed by cooling as described above can be repeated one or more times to further increase crystallinity. In a further embodiment, the heat treated stent is cooled below ambient temperature to lock in the crystals or terminate crystallization for 1 minute to 96 hours, more preferably 24 hours to 72 hours.

In one embodiment, the wet glass transition temperature of the biodegradable stent material is greater than 37° C., preferably greater than 45° C., more preferably greater than 65° C.

The treated stent or other endoprosthesis can be crimped onto a delivery balloon using mechanical crimpers comprising of wedges such as crimpers from Machine Solutions, Fortimedix, or others. The stent can also be crimped by placing the stent in a shrink tube and stretching the shrink tube slowly at a rate of 0.1 to 2 inches/minutes, more preferably 0.2 to 0.5 inches/minutes until the stent is crimped to the desired crimped diameter. During crimping, the stent is heated to a temperature of 20° C. below the Tg to 10° C. above the Tg for 30 minutes, more preferably to 10° C. below the Tg to Tg, and most preferably at the Tg of the stent material. This process facilitates or enables the stent to maintain the final crimped diameter. After crimping, the ability for the stent to remain the crimped diameter can further be improved by fixing the stent in the crimped diameter while exposing it to a temperature of 20° C. below the Tg to 10° C. above the Tg for 30 minutes, more preferably to 10° C. below the Tg to Tg, and most preferably at the Tg of the stent material, for 1 minute to 24 hours, more preferably 15 minutes to 1 hour. After holding at this crimping temperature, it is preferred to fix the stent in the crimped diameter while at or below ambient temperatures until further processing (i.e., sterilization). The stent can either be crimped while it is on the balloon of the stent delivery catheter or first crimped alone and then slipped onto the balloon of the catheter. In a further embodiment, the crimped stent is cooled below ambient temperature to lock in the crystals or terminate crystallization for 1 minute to 96 hours, more preferably 24 hours to 72 hours.

In a preferred embodiment, the final crimped stent on the catheter is sterilized by 25 to 30 kGy dose of ebeam, typically with a single dose of 30 kGy or with multiple smaller doses (eg. 3×10 kGy). The stent system is usually kept below ambient temperature before, during and/or after multiple smaller doses of sterilization. The stent that has been packaged and sterilized can also be exposed to heat treatment like that described above. In one embodiment, the biodegradable polymer stent is heated at about the Tg of the biodegradable stent material during expansion of the stent. The temperature during expansion can range from 10° C. above Tg to 10° C. below Tg.

Upon deployment of such stent, the processes provide means to minimize stent recoil to less than 10% after expansion from the crimped state to an expanded state.

Additives can be added to the endoprosthesis to affect strength, recoil, or degradation rate, or combinations thereof. Additives can also affect processing of biodegradable stent material, radiopacity or surface roughness or others. Additives can be biodegradable or non-biodegradable. The additives can be incorporated in to the biodegradable stent or polymer material by blending, extrusion, injection molding, coating, surface treatment, chemical treatment, mechanical treatment, stamping, or others or combinations thereof. The additives can be chemically modified prior to incorporation in to the biodegradable stent material.

In one embodiment, the percentage in weight of the additives can range from 0.01% to 25%, preferably 0.1% to 10%, more preferably 1% to 5%.

In one embodiment, the additive includes at least nanoclay, nanotubes, nanoparticles, exfoliates, fibers, whiskers, platelets, nanopowders, fullerenes, nanospheres, zeolites, polymers or others or combination thereof. In the present invention, the stent material may include pharmacological agents, such as immunomodulators anti-cancer, anti-proliferative, anti-inflammatory, antithrombotic, antiplatelet antifungal antidiabetic, antihyperlipidimia, antiangiogenic, angiogenic, antihypertensive, healing promoting drugs, or other therapeutic classes of drugs or combination thereof. Illustrative immunomodulators agents include but are not limited to rapamycin, everolimus, ABT 578, AP20840, AP23841, AP23573, CCI-779, deuterated rapamycin, TAFA93, tacrolimus, cyclosporine, TKB662, myriocin, their analogues, pro-drug, metabolites, slats, or others or combination thereof. Illustrative anticancer agents include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene hcl, bleomycin sulfate, busulfan, buthionine sulfoximine, BWA 773U82, BW 502U83.HCl, BW 7U85 mesylate, ceraccmide, carbetimer, carboplatin, carmustine, chlorambucil, chloroquinoxalinesulfonamide, chlorozotocin, chromomvcin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde dihydro-5-azacytidine doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrozole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydroxyurea, idarubicin HCl, ifosfamide, interferon alfa, interferon beta, interferon gamma, interleukin-1 alpha and beta, interleukin-3, interleukin-4. interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus calmetteguerin*, methotrexate, N-Methylformamide, mifepristone, mitoguazone, mitomycin-C, mitotane, mitoxantrone hydrochloride, monocyte/macrophage colony-stimulating, factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, QP-2, epothilone D, epothilone C Taxol, such as, paclitaxel, docetaxel, ABJ879, patupilone, MN-029, BMS247550, ecteinascidins such as ET-743, tetrahydroisoquinoline alkaloid, sirolimus, actinomycin, methotrexate, antiopeptin, vincristine, mitomycin, 2-chlorodeoxyadenosine or others, antifungal agents such as caspofungin, farnesylated dibenzodiazepinone, ECO-4601, fluconazole, or others, angiogenesis drugs such as follistatin, leptin, midkine, angiogenin, angiopoietin-1, becaplermin, Regranex, anti-angiogenesis drugs such as canstatin, angiostatin, endostatin, retinoids, tumistatin, vasculostatin, angioarrestin, vasostatin, bevacizumab, prinomastat, or others, antidiabetic drugs such as metformin, hypertension drugs such as candesartan, diovan, diltiazem, atenolol, adalat or others, anti-ischemic drugs such as ranolazine, isosorbide dinitrate, or others.

Examples of nanoclay includes Montmorillonite, Smectites, Talc, or platelet-shaped particles, modified clay or others or combination thereof. Clays can be intercalated or exfoliated. Example of clays include Cloisite NA, 93A, 30B, 25A, 15A, 10A or others or combination thereof.

Examples of fibers include cellulose fibers such as Linen, cotton, rayon, acetate; proteins fibers such as wool or silk; plant fiber; glass fiber; carbon fiber; metallic fibers; ceramic fibers; absorbable fibers such as polyglycolic acid, polylactic acid, polyglyconate or others.

Examples of whiskers include hydroxyapetite whiskers, tricalcium phosphate whiskers or others.

In another embodiment, the additives includes at least modified starch, soybean, hyaluronic acid, hydroxyapatite, tricarbonate phosphate, anionic and cationic surfactants such as sodium docecyl sulphate, triethylene benzylammonium chloride, pro-degradant such as D2W (from Symphony Plastic Technologies), photodegradative additives such as UV-H (from Willow Ridge Plastics), oxidative additives such as PDQ (from Willow Ridge Plastics), TDPA, family of polylactic acid and its random or block copolymers or others.

In another embodiment, the additive can induce degradation of non-degradable polymeric stent material. For example, pro-degradant such as D2W (from Symphony Plastic Technologies), photodegradative additives such as UV-H (from Willow Ridge Plastics), oxidative additives such as PDQ (from Willow Ridge Plastics), TDPA or others or combination thereof can initiate degradation of non degradable stent materials such as polyethylene, polypropylene, polyethylene terephthalate or others.

In one embodiment, additives can be incorporated into the biodegradable polymer stent material to resist oxidative degradation, photodegradation, high energy exposure degradation, thermal degradation, hydrolytic degradation, acid buildup or other degradation means. Examples of additives which resist degradation include antioxidants such as vitamin C, peroxides; stabilizers such as xanthum gum, succinoglycan, carrageenan, propylene glycol alginate; getters such as titanium containing beads, aluminium oxide; anhydrous calcium chloride, anhydrous sodium bicarbonate, anhydrous sodium sulphate, anhydrous magnesium sulphate.

In another embodiment, the additives include electroactive or electrolyte polymers, hydroscopic polymers, dessicants, or others.

In one embodiment, the additive is an oxidizer such an acids, perchlorates, nitrates, permanganates, salts or other or combination thereof.

In one embodiment, the additive is a monomer of the biodegradable polymeric stent material. For example glycolic acid is an additive to polyglycolic acid or its copolymer stent material.

In one embodiment, the additive can be water repellent monomers, oligomers or polymers such as bees wax, low MW polyethylene or others.

In another embodiment, the additive can be water attractant monomers, oligomers or polymers such as polyvinyl alcohol, polyethylene oxide, glycerol, caffeine, lidocaine or other.

In one embodiment, the additive can affect crystallinity of the biodegradable polymeric stent material. Example of additive of nanoclay to PLLA affects its crystallinity.

In the present invention, the stent material may include pharmacological agents, such as immunomodulators, anticancer, anti-proliferative, anti-inflammatory, antithrombotic, antiplatelet, antifungal, antidiabetic, antihyperlipidemic, antiangiogenic, angiogenic, antihypertensive, healing promoting drugs, or other therapeutic classes of drugs or combination thereof. Use of analogues, prodrugs, derivatives, precursors, fragments, salts, or other modifications or variations of pharmaceutical agents are all included.

Illustrative immunomodulators agents include but are not limited to rapamycin, everolimus, ABT 578, AP20840, AP23841, AP23573, CCI-779, deuterated rapamycin, TAFA93, tacrolimus, cyclosporine, TKB662, myriocin, their analogues, pro-drug, metabolites, salts, or others or combination thereof.

Illustrative anticancer agents include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus calmette*-guerin (BCG), Baker's Antifol (soluble), beta-2'-deoxythioguanosine, bisantrene HCl, bleomycin sulfate, busulfan, buthionine sulfoximine, BWA 773U82, BW 502U83.HCl, BW 7U85 mesylate, caracemide, carbetimer, carboplatin, carmustine, chlorambucil, chloroquinoxalinesulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflomithine, Elliott's® solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus calmette*-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, PALA (N-(phosphonoacetyl)-L-aspartic acid), pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, QP-2, epothilone D, epothilone C, Taxol®, paclitaxel, docetaxel, ABJ879, patupilone, MN-029, BMS247550, ecteinascidins such as ET-743, tetrahydroisoquinoline alkaloid, sirolimus, actinomycin, methotrexate, antiopeptin, vincristine, mitomycin, 2-chlorodeoxyadenosine and others.

Illustrative antifungal agents include caspofungin, farnesylated dibenzodiazepinone, ECO-4601, fluconazole, and others. Illustrative angiogenesis drugs include follistatin, leptin, midkine, angiogenin, angiopoietin-1, becaplermin, Regranex®, and others. Illustrative anti-angiogenesis drugs include canstatin, angiostatin, endostatin, retinoids, tumistatin, vasculostatin, angioarrestin, vasostatin, bevacizumab, prinomastat, and others. Illustrative antidiabetic drugs include metformin and others. Illustrative anti-hypertension drugs include candesartan, diovan, diltiazem, atenolol, adalat and others. Illustrative anti-ischemia drugs include ranolazine, isosorbide dinitrate, and others.

Illustrative antiinflammatory agents include classic nonsteroidal anti-inflammatory drugs (NSAIDS), such as aspirin, diclofenac, indomethacin, sulindac, ketoprofen, flurbiprofen, ibuprofen, naproxen, piroxicam, tenoxicam, tolmetin, ketorolac, oxaprozin, mefenamic acid, fenoprofen, nabumetone (Relafen®), acetaminophen (Tylenol®), and others; COX-2 inhibitors, such as nimesulide, NS-398, flosulide, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and others; glucocorticoids, such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, fluticasone propionate, piroxicam, celeoxib, mefenamic acid, tramadol, meloxicam, methyl prednisone, pseudopterosin, and others; anti-hypercalcemia drugs, such as zoledronic acid, alendronate and others; antithrombosis drugs, such as Plavix®, heparin, Arixtra®, Fraxiparine®, and others.

Analogs, derivatives, prodrugs, salts, or synthetic or biologic equivalents of these pharmaceutical agents can be released from the stents depending on the type of treatment needed, such as hyperproliferative diseases, stenosis, wound healing, cancer, aneurysm, diabetic disease, abdominal aortic aneurysm, angiogenesis, hypercalcemia, ischemia, fibrillation, arrhythmia or others.

The agents can be released from the implant using non-degradable, partially degradable or fully degradable coatings, or a combination thereof. The agents can be incorporated as a matrix with the coating or applied on the stent and covered with the coating as a rate limiting barrier, or the agents can be directly coated onto the stent surface.

The solvent used to incorporate the agent and the coating on a stent can be an organic solvent such as dichloromethane, tetrahydrofuran, ethanol, or other solvents. In one embodiment, the solvent used to coat the agent and/or agent-polymer matrix does not affect the chemical or mechanical properties of the polymeric stent material.

In one embodiment, supercritical fluids such as supercritical carbon dioxide is used as a carrier solvent for the agent and/or the polymer and coats the stent with the agent and/or agent-polymer matrix. The use of non-reactive gas such as carbon dioxide removes the need to use other organic solvents which can alter chemical and physical properties of the pharmacological agent.

In one embodiment the crystallinity of the pharmaceutical agent on the stent material is greater than 90%, preferably greater than 93%, more preferably greater than 95%.

In one embodiment, the pharmacological agent can be incorporated in the biodegradable polymeric stent material and extruded into stent tubing prior to laser cutting of the stent from the tubes. In another embodiment the agent is incorporated in a protective coating to prevent degradation of the agent during extrusion or laser cutting.

In one embodiment, the rate of agent release can be configured to release the agent at certain times and for certain durations corresponding to the degradation rate of the stent material or biological response events within the stent material environment. For example, an anti-inflammatory, anti-proliferative, or immunomodulator drug or a combination of these can be made to be released during the entire degradation period. Multiple drugs can be released to match the degradation rate of the coating and/or degradation rate of the implant. Antiplatelet or anti-thrombotic agents can be released in an initial phase and anti-inflammatory, antiproliferative or immunosuppressive agents can be released concurrently or at a later phase.

In another embodiment, the biodegradable polymeric stent material can have increased crystallinity by cross-linking such as exposure to radiation such as gamma or ebeam. The cumulative radiation dose can range from 1 kGray to 1000 KGray, preferably 5 to 100 KGray, more preferably 10 to 30 KGray.

An aspect of the invention provides for degradable materials having sufficient strength and low recoil for stent applications.

In one embodiment, yield strength for the biodegradable polymeric stent material is at least 50% of ultimate strength, preferably at least 75% of ultimate strength, more preferably at least 90% of ultimate strength, in water at 37° C.

In one embodiment, the elastic modulus for the biodegradable metallic stent material is at least 50 GPa, preferably at least 100 GPa, more preferably at least 150 GPa.

In another embodiment, the elastic modulus for the biodegradable polymeric stent material is at least 0.5 GPa, preferably at least 0.75 GPa, more preferably at least 1 GPa, in water at 37° C.

In one embodiment, the yield strain for the biodegradable polymeric stent material is at most 10%, preferably at most 5%, more preferably at most 3%, in water at 37° C.

In one embodiment, the plastic strain for the biodegradable polymeric stent material is at least 20%, preferably at least 30%, more preferably at least 40%, in water at 37° C.

In one embodiment, the elastic recovery of the strained biodegradable polymeric stent material is at most 15%, preferably at most 10%, more preferably at most 5%, in water at 37° C.

In one embodiment, the biodegradable stent material degrades substantially within 2 years, preferably within 1 year, more preferably within 9 months.

In one embodiment, the expanded biodegradable stent in physiological conditions at least after 1 month retains at least 25%, preferably at least 40%, more preferably at least 70% of the strength or recoil In one embodiment, the biodegradable polymeric stent materials degrades by at least bulk erosion, surface erosion, or combination thereof.

In one embodiment, the biodegradable polymeric stent material degrades by at least hydrolytic degradation, enzymatic degradation, oxidative degradation, photo degradation, degradation under physiological environment or combination thereof.

The biodegradable polymeric stent material can have varying molecular architecture such as linear, branched, crosslinked, hyperbranched or dendritic.

The biodegradable polymeric stent material in this invention can range from 10 KDa to 10,000 KDa in molecular weight, preferably from 100 KDa to 1000 KDa, more preferably 300 KDa to 600 KDa.

In one embodiment, the biodegradable polymeric stent material is a polymer with a molecular weight equal or greater than the threshold molecular weight of the polymer. In one embodiment, the biodegradable polymeric stent material with molecular weight equal to or greater than the threshold molecular weight provide strength greater than a biodegradable polymeric stent with molecular weight lower than the threshold molecular weight.

In another embodiment, the biodegradable stent material has increased crystallinity by increasing orientation of polymer chains with in the biodegradable stent material in radial and/or longitudinal direction by drawing, pressurizing and/or heating the stent material. In another embodiment, the drawing, pressurizing and/or heating the stent material occurs simultaneously or sequentially.

In one embodiment, the biodegradable stent material is placed with at least one surface against a non deformable surface and is pressurized to at least 200 psi, preferably to at least 300 psi, more preferably to at least 500 psi. In another embodiment, the biodegradable stent material is pressurized to at least 200 psi, preferably to at least 300 psi, more preferably to at least 500 psi.

In one embodiment, the biodegradable stent material tube is placed with in a larger diameter non deformable tube and is pressurized to at least 200 psi, preferably to at least 300 psi, more preferably to at least 500 psi. In another embodiment, the biodegradable stent material tube is pressurized to at least 200 psi, preferably to at least 300 psi, more preferably to at least 500 psi.

In one embodiment, the biodegradable stent material has increased crystallinity by increasing the orientation of the polymer chains by at least heating the biodegradable stent material above its glass transition temperature (Tg) and below its melting temperature.

In one embodiment, the biodegradable stent material has increased crystallinity by heating the material to a temperature at least 10° C. higher than its Tg, preferably at least 20° C. higher, more preferably at least 30° C. higher than the Tg of the biodegradable stent material.

In one embodiment, biodegradable stent material has increased crystallinity after drawing, heat and/or pressurizing and annealing at elevated temperature with or without vacuum. In one embodiment, the annealing temperature is below the temperature used for orientation of the polymer chains of the biodegradable stent material. In another embodiment, the annealing temperature is at most 20° C. below, preferably at most 15° C. below, more preferably at most 10° C. below the temperature for orientation of the polymer chains of the biodegradable stent material.

In one embodiment, the biodegradable stent material after annealing is quenched below Tg of the biodegradable stent material, preferably at least 25° C. below Tg, more preferably at least 50° C. below Tg of the biodegradable stent material.

In one embodiment, the biodegradable polymeric stent material has increased crystallinity by using a combination of solvents, with one solvent having solubility parameter with in 10% of the solubility parameter of the polymer and the second solvent having solubility parameter at least 10% different than the solubility parameter of the polymer in the solvent.

In one embodiment the biodegradable polymer stent material has a crystallinity of greater than 10%, preferably greater than 25%, more preferably greater than 50%.

In another embodiment the biodegradable polymer stent material has a crystallinity of greater than 20%, preferably greater than 40%, more preferably greater than 60%.

The invention also provides means to improve consistency of strength, recoil or degradation rate of a biodegradable polymer stent material.

In another embodiment, the percentage impurity of the biodegradable polymer stent material is equal or less than 3%, preferably less than 1%, more preferably less than 0.1%.

In another embodiment, the percentage residual monomer or oligomer of the biodegradable polymer stent material is equal or less than 3%, preferably less than 1%, more preferably less than 0.1%.

The invention also provides means to improve shelf life of a biodegradable polymer stent material. In one embodiment, the shelf life of the biodegradable stent material is extended by packaging in an environment of at least low moisture, low oxygen, low UV, low temperature, nitrogen, vacuum or other, or a combination thereof.

Example

Figure 4:
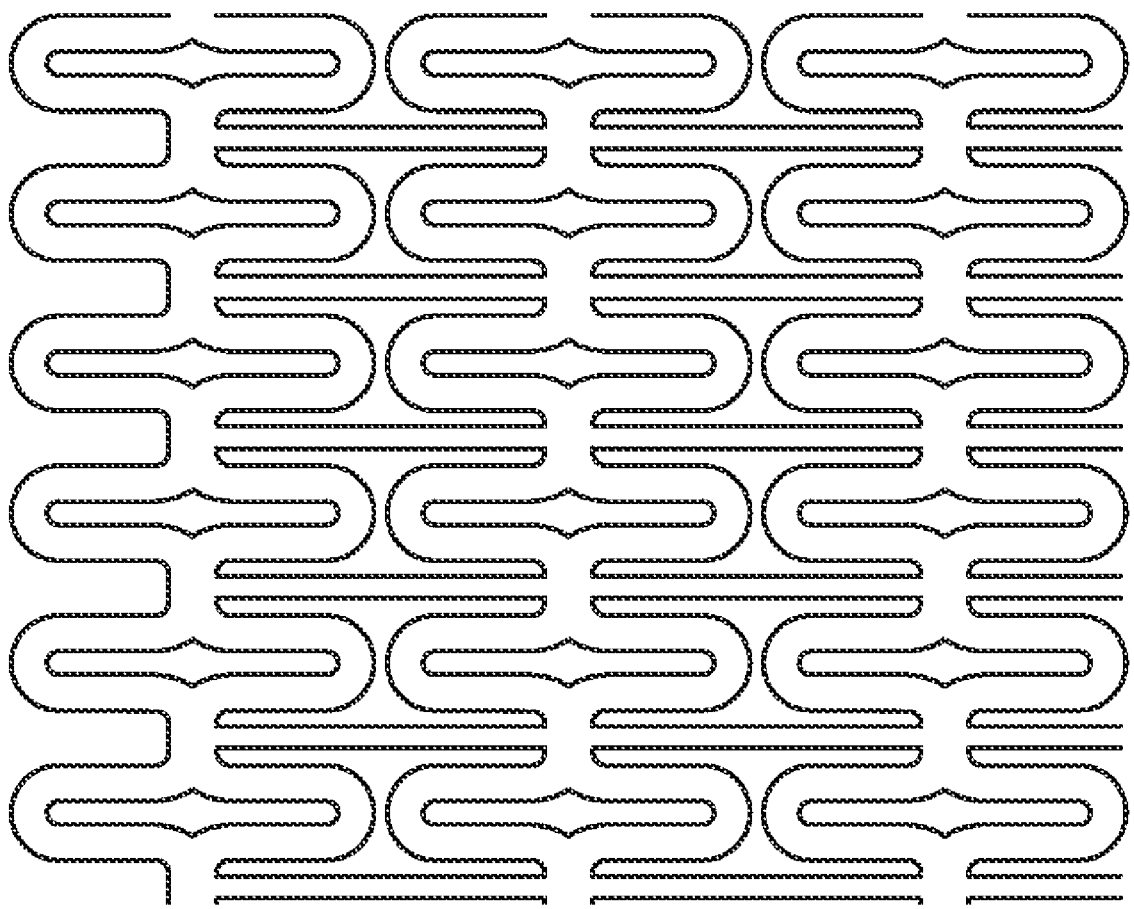
FIG. 4 illustrates a stent pattern utilized in an Example of the present application.

A tube is made by spraying an amorphous copolymer poly (L-lactide-co-glycolide) with 85% lactide and 15% glycolide. The polymer and rapamycin analog can be dissolved in a solvent and can be sprayed together to incorporate the rapamycin into the polymer stent. A mandrel is placed underneath an ultrasonic spray nozzle (Micromist System with Ultrasonic Atomizing Nozzle Sprayer, Sono-Tek, N.Y.) which is rotating at 80 rpm and move longitudinally at a rate of 0.050 inches/minutes. A solution of 11 to 1 ratio of poly (L-lactide-co-glycolide) and rapamycin analog on the mandrel. The resulting tube has a thickness of 0.17 mm. The tube is heated at 45° C. for about 60 hours, annealed at 90° C. for 2 hours, and cooled to ambient or room temperature with in 10 seconds. The annealed tube is then cut with a UV laser to the design shown in FIG. 4 (shown in its crimped state). The cut stent is annealed at 90° C. and slowly cooled from the annealing temperature to ambient temperature within eight hours. The stent delivery system is then packaged in a pouch and sterilized by gamma radiation.

The heat treated stent has higher radial strength than the non-treated stent (Table 1).

TABLE 1

Comparison of Radial Strength of Treated and Non-treated Stent.

| Type | No Heat Treatment | Heat Treatment |
|---|---|---|
| Radial Strength After Laser Cutting Stent | 7 Psi | 14 Psi |
| Radial Strength After Crimping Stent | 6 Psi | 9 Psi |
| Radial Strength After 30kGy Ebeam Sterilization | 3 Psi | 8 Psi |
| Radial Strength when expanded at Tg | n/a | 12.5 Psi |

Thus, as shown in FIG. 1, methods according to the present invention initially provide for a tubular body composed of an amorphous polymer, where the tubular body may be formed by extrusion, molding, dipping, or the like, but is preferably formed by spraying onto a mandrel. The tubular body is annealed to increased crystallinity and strength, usually by the heating and cooling processes described above. The tubular body is then patterned to form a stent or other endoprosthesis, typically by laser cutting, usually after at least one annealing treatment. Optionally, the tubular body may be treated both before and after patterning, and may be treated by annealing more than once both before and after the patterning.

Figure 2A:
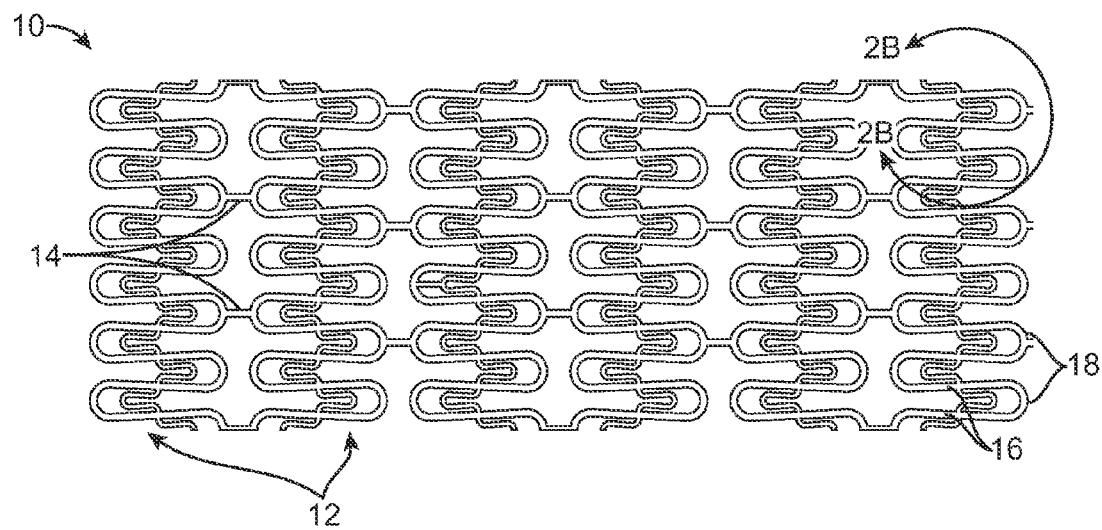
FIGS. 2A and 2B illustrate an exemplary stent structure which may be fabricated using the methods of the present invention.
Figure 2B:
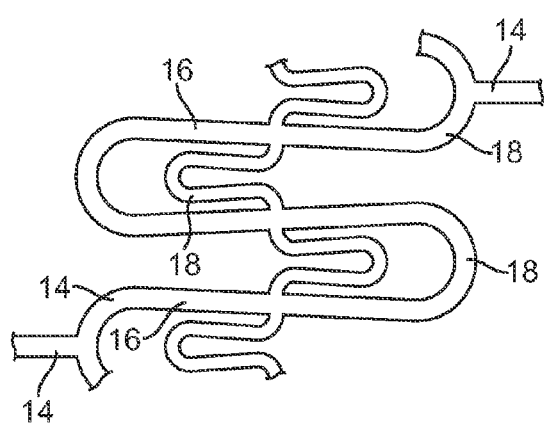
Figure 3:
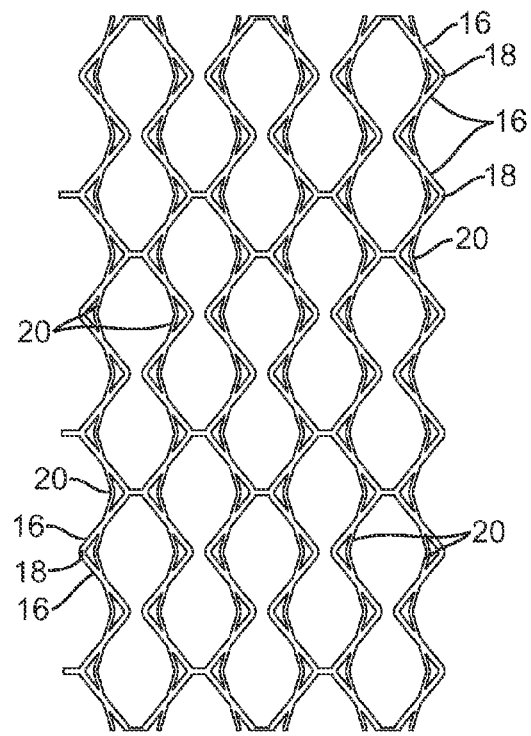
FIG. 3 illustrates the stent of FIGS. 2A and 2B in a radially expanded configuration.

Referring now to FIGS. 2A and 2B, a stent 10 suitable for modification by the present invention has base pattern including a plurality of adjacent serpentine rings 12 joined by axial links 14. As illustrated, the stent 10 includes six adjacent serpentine rings 12, where each ring includes six serpentine segments comprising a pair of axial struts 16 joined by a hinge-like crown 18 at one end. The number of rings and segments may vary widely depending on the size of the desired size of the stent. According to the present invention, a supporting feature 20 is disposed between adjacent axial struts 16 and connected so that it will expand, usually elongate, circumferentially with the struts, as shown in FIG. 3. The supporting features 20 are in a generally closed U-shaped configuration prior to expansion, as shown in FIGS. 2A and 2B, and open into a shallow V-shape along with the opening of the axial struts 16 about the crowns 18 during radial expansion of the serpentine rings 12, as shown in FIG. 3. Supporting features 20 enhance the hoop strength of the stent after radial expansion, help resist recoil after expansion is completed, and provide additional area for supporting the vascular or other luminal wall and optionally for delivering drugs into the luminal wall.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A biodegradable stent prosthesis comprising,
a tubular body comprising a biodegradable polymeric material, wherein said tubular body has been formed using extrusion, molding, dipping, or spraying and has been treated, said biodegradable polymeric material is substantially amorphous after said treatment and has a $T_g$ greater than 37° C., and the stent prosthesis at 37° C. is radially expandable and has sufficient strength to support a blood vessel.

2. A biodegradable stent prosthesis comprising:
a tubular body comprising a biodegradable polymeric material, wherein said tubular body has been formed using extrusion, molding, dipping, or spraying and has been treated, said biodegradable polymeric material has a crystallinity of 10% to 30% after said treatment and has a Tg greater than 37° C., and the stent prosthesis at 37° C. is radially expandable and has sufficient strength to support a blood vessel.

3. A biodegradable stent prosthesis as in claim 1 or 2, wherein the biodegradable polymeric material comprises a biodegradable polymer selected from the group consisting of poly-DL-Lactide, polylactide-co-glycolide, polylactide-co-polycaprolactone, poly (L-lactide-co-trimethylene carbonate), polytrimethylene carbonate and copolymers thereof; polyhydroxybutyrate and copolymers thereof; polyhydroxyvalerate and copolymers thereof; poly orthoesters and copolymers thereof; poly anhydrides and copolymers thereof; polylactide and copolymers thereof; polyglycolides and copolymers thereof; polycaprolactone and copolymers thereof; and polyiminocarbonates and copolymers thereof.

4. A biodegradable prosthesis as in claim 3, wherein the polymer comprises a copolymer of L-lactide and glycolide.

5. A biodegradable prosthesis as in claim 4, wherein the copolymer comprises 85% L-lactide and 15% glycolide by weight.

6. A biodegradable stent prosthesis as in claim 3, wherein the biodegradable polymer is polylactide-co-glycolide or polylactide-co-polycaprolactone.

7. A biodegradable stent prosthesis as in claim 3, wherein the biodegradable polymer is a copolymer comprising poly-L-lactide.

8. A biodegradable stent prosthesis as in claim 3, wherein the biodegradable polymer is a homopolymer, copolymer, graft polymer, block polymer, or a blend of two or more homopolymers or copolymers.

9. A biodegradable stent prosthesis as in claim 3, wherein the biodegradable polymer is a copolymer of polycaprolactone.

10. A biodegradable stent prosthesis as in claim 3, wherein the biodegradable polymer is a polylactide-co-polycaprolactone polymer, a blend of a polylactide polymer and a polycaprolactone polymer, a polylactide-co-glycolide polymer, or a blend of a polylactide polymer and a glycolide polymer.

11. A biodegradable stent prosthesis as in claim 1 or 2, wherein the treatment comprises at least one cycle of heating and cooling.

12. A biodegradable stent prosthesis as in claim 11, wherein the treatment comprises at least two cycles of heating and cooling.

13. A biodegradable stent prosthesis as in claim 1 or 2, wherein the treatment comprises exposure to radiation.

14. A biodegradable stent prosthesis as in claim 13, wherein the radiation is gamma or e-beam radiation.

15. A biodegradable stent prosthesis as in claim 1 or 2, wherein the biodegradable polymeric material comprises less than 3% monomer content.

16. A biodegradable stent prosthesis as in claim 1 or 2, wherein the treatment comprises at least one of heating, cooling, pressurizing, addition of an additive, drawing in radial and/or longitudinal direction, cross linking, and exposure to radiation.

17. A biodegradable stent prosthesis as in claim 16, wherein the additive is selected from the group consisting of nanoclay, nanotubes, nanoparticles, exfoliates, fibers, whiskers, platelets, nanopowders, fullerenes, nanospheres, and zeolites.

18. A biodegradable stent prosthesis as in claim 1 or 2, wherein the prosthesis degrades substantially within 2 years.

19. A biodegradable stent prosthesis as in claim 1 or 2, wherein the biodegradable polymeric material after the treatment has one or more properties selected from the group consisting of a yield strength of at least 50% of ultimate strength in water at 37° C., an elastic modulus of least 0.5 GPa in water at 37° C., a yield strain of at most 10% in water at 37° C., and a plastic strain of at least 20% in water at 37° C.

20. A biodegradable stent prosthesis as in claim 1 or 2, wherein the biodegradable polymeric material after the treatment has a yield strain of at most 10% in water at 37° C. and a plastic strain of at least 20% in water at 37° C.

21. A biodegradable stent prosthesis as in claim 1 or 2, wherein the stent prosthesis has a radial strength of at least 8 psi.

22. A biodegradable stent prosthesis as in claim 1 or 2, wherein the stent prosthesis after the treatment has increased strength and period of biodegradation for the prosthesis is not substantially lengthened.

23. A biodegradable stent prosthesis as in claim 1 or 2, wherein the biodegradable polymeric material after the treatment has a molecular weight from 100 KDa to 1000 KDa.

24. A biodegradable stent prosthesis as in claim 1 or 2, wherein the stent prosthesis further comprises a drug.

25. A biodegradable stent prosthesis as in claim 24, wherein the drug inhibits restenosis of a blood vessel.

26. A biodegradable stent prosthesis as in claim 24, wherein the drug is rapamycin, everolimus, ABT 578, AP20840, AP23841, AP23573, CCI-779, deuterated rapamycin, TAFA93, tacrolimus, cyclosporine, TKB662, myriocin, paclitaxel, their analogues, pro-drug, metabolites, salts, or combination thereof.

27. A biodegradable stent prosthesis as in claim 1 or 2, wherein the stent prosthesis further comprises an additional biodegradable polymer.

28. A biodegradable stent prosthesis as in claim 1 or 2, wherein the tubular body further comprises a drug.

29. A biodegradable stent prosthesis of claim 1 or 2 wherein the tubular body has a diameter of about 1-1.5 times an intended deployment diameter of the stent prosthesis.

30. A biodegradable stent prosthesis as in claim 1 or 2, wherein the treatment increases crystallinity of the biodegradable polymeric material by at least 20% of the original crystallinity.

31. A biodegradable stent prosthesis as in claim 1 or 2, wherein the stent prosthesis has a radial strength of at least 3 psi.

32. A biodegradable stent prosthesis as in claim 1 or 2, wherein the stent prosthesis retains at least 25% of strength after at least 1 month in physiological conditions.

33. A biodegradable stent prosthesis as in claim 1 or 2, wherein the stent prosthesis retains at least 40% of strength after at least 1 month in physiological conditions.

34. A biodegradable stent prosthesis as in claim 1 or 2, wherein the stent prosthesis retains at least 70% of strength after at least 1 month in physiological conditions.

35. A biodegradable stent prosthesis as in claim 1 or 2, wherein the tubular body is patterned into the stent prosthesis.

36. A biodegradable stent prosthesis as in claim 35, wherein the tubular body is patterned at an expanded diameter.

37. A biodegradable stent prosthesis as in claim 36, wherein the diameter is larger than a crimped diameter.

38. A biodegradable stent prosthesis as in claim 35, wherein the tubular body is patterned at an expanded diameter about 1 to 1.3 times larger than an intended deployed diameter of the stent prosthesis.

39. A biodegradable stent prosthesis as in claim 35, wherein the tubular body is patterned before or after the treatment.

40. A biodegradable stent prosthesis as in claim 35, wherein the tubular body undergoes the treatment before or after patterning.

41. A biodegradable stent prosthesis as in claim 35, wherein the patterned tubular body is balloon expandable.

42. A biodegradable stent prosthesis as in claim 35 having a diameter of about 1 to 1.5 times of an intended deployment diameter of the stent prosthesis.

43. A biodegradable stent prosthesis as in claim 35, wherein the stent prosthesis has a diameter that is substantially the same as the initial diameter of the tubular body.

44. A biodegradable stent prosthesis as in claim 35, wherein the stent prosthesis is crimped to a diameter smaller than an intended deployment diameter of the stent prosthesis.

45. A biodegradable stent prosthesis as in claim 44, wherein the stent prosthesis has a diameter of about 1 to 1.5 times the intended deployment diameter of the stent prosthesis.

46. A biodegradable stent prosthesis as in claim 1 or 2, wherein said stent prosthesis has a recoil from an expanded condition of less than 10%.

47. A biodegradable stent prosthesis as in claim 1 or 2, wherein said stent prosthesis has a yield strain of at most 10% and a plastic strain of at least 20%.

48. A biodegradable stent prosthesis as in claim 1 or 2, wherein said tubular body has been treated in a substantially amorphous state.

49. A biodegradable stent prosthesis as in claim 1 or 2 wherein the tubular body has an initial diameter.

50. A biodegradable stent prosthesis as in claim 49 wherein the initial diameter of the tubular body is about 1 to 1.5 times of an intended deployment diameter of the stent prosthesis.

51. A biodegradable stent prosthesis as in claim 49, wherein the tubular body after treatment has a diameter that is substantially the same as the initial diameter of the tubular body.

52. A biodegradable stent prosthesis as in claim 1 or 2, wherein the stent prosthesis has one or more properties selected from the group consisting of a yield strength of at least 50% of ultimate strength in water at 37° C., an elastic modulus of least 0.5 GPa in water at 37° C., a yield strain of at most 10% in water at 37° C., and a plastic strain of at least 20% in water at 37° C.

53. A biodegradable stent prosthesis as in claim 1 or 2, wherein the treatment comprises one or more treatments.

54. A biodegradable stent prosthesis as in claim 1 or 2, wherein the stent prosthesis is expandable at body temperature from a crimped configuration.

* * * * *